United States Patent
Sievers et al.

(10) Patent No.: US 6,229,053 B1
(45) Date of Patent: May 8, 2001

(54) METHOD FOR PURIFICATION OF FORMALDEHYDE, USE THEREOF AND PLASTICS PRODUCED THEREWITH

(75) Inventors: Werner Sievers, Frankfurt; Elke Schweers, Bad Soden; Christine Meister, Sulzbach, all of (DE)

(73) Assignee: Ticona GmbH (DE)

(*) Notice: Subject to any disclaimer, the term of this patent is extended or adjusted under 35 U.S.C. 154(b) by 0 days.

(21) Appl. No.: 09/530,442

(22) PCT Filed: Oct. 12, 1998

(86) PCT No.: PCT/EP98/06440

§ 371 Date: May 25, 2000

§ 102(e) Date: May 25, 2000

(87) PCT Pub. No.: WO99/23054

PCT Pub. Date: May 14, 1999

(30) Foreign Application Priority Data

Oct. 31, 1997 (DE) ............................................. 197 48 380

(51) Int. Cl.⁷ .................................................... C07C 45/00
(52) U.S. Cl. .......................... 568/493; 568/422; 568/449; 568/457; 568/458; 568/465

(58) Field of Search ..................................... 568/422, 449, 568/457, 458, 465, 493

(56) References Cited

FOREIGN PATENT DOCUMENTS

1518352 * 3/1968 (FR) .
 987457 * 3/1965 (GB) .
1138426 * 1/1969 (GB) .

* cited by examiner

*Primary Examiner*—Sreeni Padmanabhan
(74) *Attorney, Agent, or Firm*—Connolly Bove Lodge & Hutz LLP

(57) ABSTRACT

Abstract A process for purifying formaldehyde in which the formaldehyde is scrubbed with alcohol in an absorption unit and in the course of this reacted virtually completely to form the hemiformal and is simultaneously separated off from gaseous impurities in a first purification step. In a desorption unit, the residual impurities are then converted into a gaseous state and separated off from the liquid hemiformal, whereupon the purified hemiformal is thermally cleaved into alcohol and formaldehyde in a pyrolysis unit. The formaldehyde thus prepared is suitable, for example, for preparing oligomers, polymers, dyestuffs and fertilizers, as well as for the treatment of seeds.

9 Claims, 1 Drawing Sheet

METHOD FOR PURIFICATION OF FORMALDEHYDE, USE THEREOF AND PLASTICS PRODUCED THEREWITH

Process for purifying formaldehyde, its use and plastics prepared using it

This application is the U.S. National Stage application of PCT/EP98/066440 filed Oct. 21, 1998.

FIELD OF THE INVENTION

The invention relates to a process for purifying formaldehyde, that is in particular for the continuous purification of formaldehyde, the use of formaldehyde purified in this manner for preparing plastics, in particular polyacetals and polyoxymethylenes, and plastics which have been prepared using the formaldehyde thus purified.

Formaldehyde is an important feedstock of the chemical synthesis of many products such as plastics, fertilizers, dyestuffs, and in mirror manufacture and textile finishing. It is therefore synthesized industrially in large amounts. Accordingly, a multiplicity of different processes for preparing formaldehyde are known, the synthesis from methanol having the greatest importance. In this synthesis, by means of an oxidative dehydrogenation, for example on an oxidized copper wire, formaldehyde is synthesized by oxidizing methanol with air. In this synthesis, 30–40 % strength aqueous solutions of formaldehyde are usually obtained, which already, from the preparation process, comprise the methanol necessary for stabilization.

DESCRIPTION OF THE PRIOR ART

German patent application 197 22 774.0 and the international patent application PCT/EP98/03084 corresponding thereto describe the preparation of formaldehyde by direct dehydrogenation of methanol at a temperature of 300 to 1000°C using a catalyst. In this process, a circulated gas stream, which predominantly consists of hydrogen and carbon monoxide, is passed through the reactor. In this manner, a mixture is formed which comprises formaldehyde, hydrogen, carbon monoxide and by-products such as water, methanol, methyl formate, methylal, carbon dioxide and methane at contents <5% by weight.

However, all these processes for preparing formaldehyde have the disadvantage that, using them, formaldehyde is not obtained as a pure substance, but as a mixture containing unwanted by-products and unreacted feedstocks. However, for a plurality of industrial syntheses, such as the preparation of engineering plastics, formaldehyde in a highly pure state is required, since the quality of the product produced using it is also dependent on the purity of the gaseous formaldehyde, in addition to the reaction conditions selected.

Therefore, a multiplicity of processes have already been developed to separate off formaldehyde from an aqueous solution and prepare high-grade products using it. In such cases, formaldehyde is customarily taken off from an aqueous solution and then further purified in the gaseous state. The underlying engineering and material properties of formaldehyde are described in J.F. Walker, "Formaldehyde", Reinhold Publishing Corporation Chapman and Hall, Ltd., London.

In addition, DE-A 10 90 191 describes a process for the continuous purification of gaseous formaldehyde, in which the formaldehyde is brought into contact with a flowing surface of a cold liquid formaldehyde/hemiacetal solution, which itself was formed by reacting formaldehyde with a primary and secondary alcohol. In this process, 60 –98% of the liquid contaminants from the formaldehyde gas are absorbed by the cold liquid solution. However, removal of substances which are usually gaseous, such as $N_2$, $O_2$, $CO_2$, and CO is not possible by this process, as is expressly emphasized.

U.S. Pat. No. 2,848,500 describes a process according to which a formaldehyde/water mixture is reacted with an alcohol whose boiling point is above 95°C to form the hemiformal, the resulting mixture is dehydrated under reduced pressure to form a hemiformal solution of considerably lower water content and is then pyrolyzed, the formaldehyde being released from the hemiformal, whereupon by partial condensation of the pyrolysis products, the alcohol is recovered as liquid and formaldehyde as vapor. However, in this process formaldehyde is removed together with water, as a result of which the yield is considerably decreased. Therefore, further process stages are required in order to recover the formaldehyde removed from the mixture and separate it off from the water. For this reason, DE-A 16 18 772teaches adding at least one alkali metal salt of an organic acid to the mixture before dewatering.

U.S.Pat. No. 3,510,525 describes a process for preparing gaseous formaldehyde, according to which a gaseous mixture of air and aqueous formaldehyde is reacted in countercurrent with a circulating dry mixture of formaldehyde and polyhydric alcohol to give the hemiacetal. The remaining gaseous mixture, which comprises unreacted formaldehyde, is reacted in a second step at a lower temperature with an aqueous formaldehyde/alcohol mixture, and finally, in a third step, the remainder of the gaseous formaldehyde still present is dissolved in water. The hemiformal solution of the first step is then fed to the pyrolysis, if appropriate after an upstream drying using solid desiccants or using dry air or another drying method. DE-A 41 37 846 describes a process for preparing substantially anhydrous and impurity-free formaldehyde from aqueous formaldehyde solutions, the aqueous solution being extracted with an alcohol, the alcoholic hemiacetal solution thus obtained being freed from water and thereafter being thermally cleaved in a subsequent solvent exchange column in the presence of a solvent having a lower boiling point than the alcohol used in the extraction and formaldehyde in a mixture with the solvent being taken off as overhead product. DE-A 12 49 846 describes the thermal decomposition of substantially pure hemiformals in columns having heated plates at temperatures between 20 and 250°C and residence times of 1 to 60 min., the hemiformal being forced along the heating surfaces by spiral internals or internals constructed as baffle plates.

DESCRIPTION OF THE PREFERRED EMBODIMENT

However, all the processes described above have disadvantages with respect to the purity of the formaldehyde obtained or in the yield, or they cannot be carried out continuously. The object therefore underlying the invention was to provide a purification process for formaldehyde which does not have the above described disadvantages and using which, even in the continuous process, formaldehyde is obtainable in a highly pure state, with formation of hemiacetals in a simple manner without significant loss of yield.

This is achieved according to the invention by the formaldehyde being scrubbed with an alcohol in an absorption unit and the formaldehyde here being virtually completely dissolved in the alcohol or converted to the hemiformal and simultaneously in a first purification step, gaseous impurities, which are not absorbed by the scrubbing solution, being separated off. The formalde-hyde/alcohol/hemiformal solution is thereafter passed to a desorption unit, in which the residual impurities absorbed in the absorption unit by the alcohol/hemiformal solution are converted into a gaseous state and thus separated off from the hemiformal. The hemiformal purified in this manner is then cleaved in a pyrolysis unit to form the alcohol and formaldehyde and the alcohol and formaldehyde are recovered. In the process according to the invention, formaldehyde is preferably purified in the gaseous state in which it arises directly on synthesis. However, it is also possible to use formaldehyde in other forms, eg. as formalin, but preferably, here also, it is first converted into the gaseous state.

As absorption unit, use is preferably made of absorption columns, in particular surface rectifiers, such as packed columns or plate columns, plate columns having a high holdup capacity and packed columns having a high surface area. Columns which are particularly preferred are bubble cap tray columns, spray columns, trickle columns and columns with a random packing. To achieve the highest possible absorption of formaldehyde, preferably, use is made of columns having internals which provide the highest possible exchange area.

The process according to the invention is preferably carried out in such a manner that the alcohol is introduced into the absorption unit in countercurrent to the formaldehyde. This is because it has been found that, in this manner, the gaseous by-products and feedstocks introduced together with the formaldehyde, in particular the hydrogen/carbon monoxide gas mixture of the circulated gas, strip out again substances absorbed by the alcohol, such as methyl formate, carbon monoxide and other components of the hemiformal solution in the upper region of the column. In this manner, it is possible to carry out the removal of circulated gas, the formation of hemiformal and a further purification of the hemiformal solution by stripping in a single apparatus. In addition, owing to this purification of the hemiformal solution, it may be possible to omit the desorption unit with appropriate process procedure in the absorption unit.

For the process according to the invention, both monohydric and polyhydric alcohols can be used, provided that their boiling point, in particular at atmospheric pressure, is markedly above that of water and markedly below the pyrolysis temperature of the hemiformal produced. To avoid further unwanted side reactions, it is preferred to use alcohols which themselves do not contain reactive groups such as carbonyl, nitro or amino groups. Particularly preferred alcohols are alcohols having 1 to 8 carbon atoms, in particular 3 to 7 carbon atoms, cyclohexanol being particularly preferred.

To avoid unwanted side reactions, formaldehyde is absorbed at temperatures above 0°C, preferably in the range from 5 to 45°C, in particular in the range from 15 to 40°C, temperatures in the range from 20 to 30°C being particularly preferred. The absorption is expediently carried out at atmospheric pressure. However, it is also possible to carry out the absorption at slightly elevated pressure or under a slightly reduced pressure. For the process according to the invention, it has proved to be expedient to carry out the absorption at temperatures as low as possible the lower limit being determined by the viscosity of the alcohol. For example, cyclohexanol at room temperature has a viscosity of $6.8 \times 10^{-2}$ Ns/m.

Since the viscosity of the alcoholic solution decreases with increasing loading of formaldehyde, ie. with increasing hemiformal concentration, it has also proved to be expedient in particular cases to introduce an alcohol/hemiformal solution into the absorption unit instead of a pure alcohol, in order in this manner to decrease the absorption temperature. Particularly expediently in this case, the alcohol recovered from the pyrolysis is admixed with the hemiformal solution purified in the desorption unit, or an incompletely cleaved alcohol/hemiformal solution from the pyrolysis unit is recycled.

In the process according to the invention, the formation of hemiformal, or the reaction temperature, is controlled via the alcohol volumetric flow rate, expediently via the alcohol input and/or the hemiformal output. It has proved to be advantageous here that the formation reaction is subjected to closed-loop control in such a manner that formaldehyde is present as hemiformal in the solution in the output area in an amount of 50 to 500 g/l, preferably 150 to 350 g/l, and in particular between 200 and 300 g/l. In the process according to the invention, neither the carbon monoxide nor hydrogen is absorbed, so that it is possible to separate off all the circulated gas from the formaldehyde in the first reaction step without further problems. Although, in this case, virtually all the formaldehyde is converted to hemiformal, the minor components are only absorbed by the alcohol/hemiformal solution to a limited extent, so that these also for the most part can be separated off in the first absorption step in the gaseous state.

The prepurified hemiformal solution discharged from the absorption unit is introduced, in accordance with the process according to the invention, into a desorption unit. In the desorption unit, the by-products absorbed or dissolved in the hemiformal/alcohol solution are converted into a gaseous state and separated off from the liquid hemiformal solution. The desorption, ie. the conversion of the dissolved impurities, is achieved in the process according to the invention by increasing the temperature and/or applying reduced pressure.

In addition, it has proved to be expedient to carry out the desorption using an inert gas, preferably using nitrogen. In principle, depending on the type of the alcohol used and the impurities present, a temperature as high as possible or reduced pressure must be used. Since however, with increasing temperature, unwanted side reactions, for example methyl formate formation, begin to an increased extent, the temperature should not exceed a defined limit value. In this manner, volatile components such as water, methanol and methyl formate are expelled, that is without significant formaldehyde losses.

At an extraordinarily high water loading, it has proved to be expedient to carry out a vacuum distillation instead of, or in addition to, the desorption unit.

At a not excessive minor component loading of the hemiformal solution exiting from the absorption unit, the desorption unit may be omitted. The hemiformal solution is then passed directly to the pyrolysis unit.

In the process according to the invention, the desorption is generally carried out at temperatures in the range from 20 to 100°C, in particular from 30 to 70 °C and preferably at 40 to 60°C and/or at a reduced pressure of 1 to 1000 mbar, in particular 10 to 500 mbar, and preferably at 20 to 100 mbar. Since the hemiformal is usually not cleaved until higher temperatures, and usually has a higher boiling point than the alcohol and the impurities, this is usually the highest-boiling component of the alcohol/hemiformal solution.

As desorption unit, use is preferably made of columns, more precisely, in particular, packed columns and also plate columns. Since the desorption unit can also be an apparatus suitable for vacuum distillation, all columns suitable for distillation have proved to be expedient. It is particularly preferred to introduce the alcohol/hemiformal solution into the upper part of the desorption unit and to introduce the inert gas in countercurrent thereto, more precisely preferably in the lower part of the column, so that the more volatile impurities can be stripped from the solution by the inert gas. This produces an additional purification effect.

The purified hemiformal discharged from the desorption column is then passed into a pyrolysis unit in which it is thermally cleaved to the formaldehyde and the alcohol. It has proved to be expedient here to select the pyrolysis conditions in such a manner that the alcohol/hemiformal solution has a residence time in the pyrolysis unit as short as possible in order to avoid unwanted side reactions, ie. the reformation of impurities.

Preferred pyrolysis units are evaporators, it being preferred to use thin-film evaporators, more precisely, preferably, those which can be operated at as high a rotary speed as possible.

When cyclohexanol is used as alcohol, it has proved to be expedient to carry out the pyrolysis in a temperature range from 100 to 200°C, preferably from 120 to 180°C and in particular at a temperature of 150 to 175°C and/or at pressures of 30 to 1500 mbar, in particular from 50 to 1300 mbar. The gas mixture discharged from the pyrolysis comprises formaldehyde and the alcohol.

Low-volatility impurities and by-products which may be present are separated off as liquid or solid in the pyrolyzer. In the discharged gas mixture, the higher-boiling alcohol is then recondensed in a condenser, if appropriate together with hemiformals, and can thus, if appropriate after further purification steps, be recirculated for further absorption and desorption operations in the process according to the invention. The non-condensed formaldehyde is obtained as a pure gas stream which is free from carbon monoxide and hydrogen and is essentially free from methanol. By means of the process according to the invention, without further problems, degrees of purity may be achieved at which the methanol content is less than 100 ppm, in particular less than 50 ppm and preferably less than 30 ppm.

The formaldehyde prepared by the process according to the invention is suitable for all known areas of use, for example corrosion protection, mirror manufacture, electrochemical coatings, for disinfection and as a preservative, and in addition as an intermediate for preparing polymers such as polyacetals, in particular polyoxymethylene, phenol resins, polyurethanes, melamine resins, aminoplastics, phenolics and casein plastics, and also 1,4-butanols, trimethylolpropane, neopentyl glycol, pentaerythritol, alcoholic formaldehyde solutions, dyestuffs, such as fuchsin and acridine, and fertilizers and also for treating seeds. Preferably, it is used for preparing said plastics.

Since formaldehyde is usually prepared with a low water content by the process according to the invention, formaldehyde prepared in this manner is suitable in particular for polymerization to polyoxymethylene and trioxane, since anhydrous formaldehyde is to be used here. The invention also relates to plastics prepared in this manner, such as polyoxymethylene and polyacetals, and trioxane, dyestuffs, fertilizers and to the treatment of seeds.

DESCRIPTION OF THE DRAWINGS

The invention is to be described in more detail with reference to the accompanying FIG. 1 which shows an apparatus for carrying out the process according to the invention.

As can be seen in FIG. 1, the absorption unit (1) constructed as column or tower has in its lower part an inlet for introducing the crude gas (2) coming from the dehydrogenation and a downstream outlet for the alcohol/hemiformal solution formed. In the upper area, the column comprises an inlet port for the alcohol and an orifice further upstream for the escape of the offgases and gaseous impurities (3). The prepurified alcohol/hemiformal solution coming from the absorption unit (1) is passed into a desorption unit (4) which is likewise constructed as column or tower. The desorption unit (4), in the lower part, has an exit port lying downstream of the process stream for the purified, ie. desorbed, alcohol/hemiformal solution and a port for introducing the inert gas (N2), which is passed through the desorption unit in countercurrent to the alcohol/hemiformal solution. At the upper end, the desorption unit has an exit port for the volatile impurities or the impurities stripped off by the inert gas, which are taken off via a compressor (5).

Figure 1:
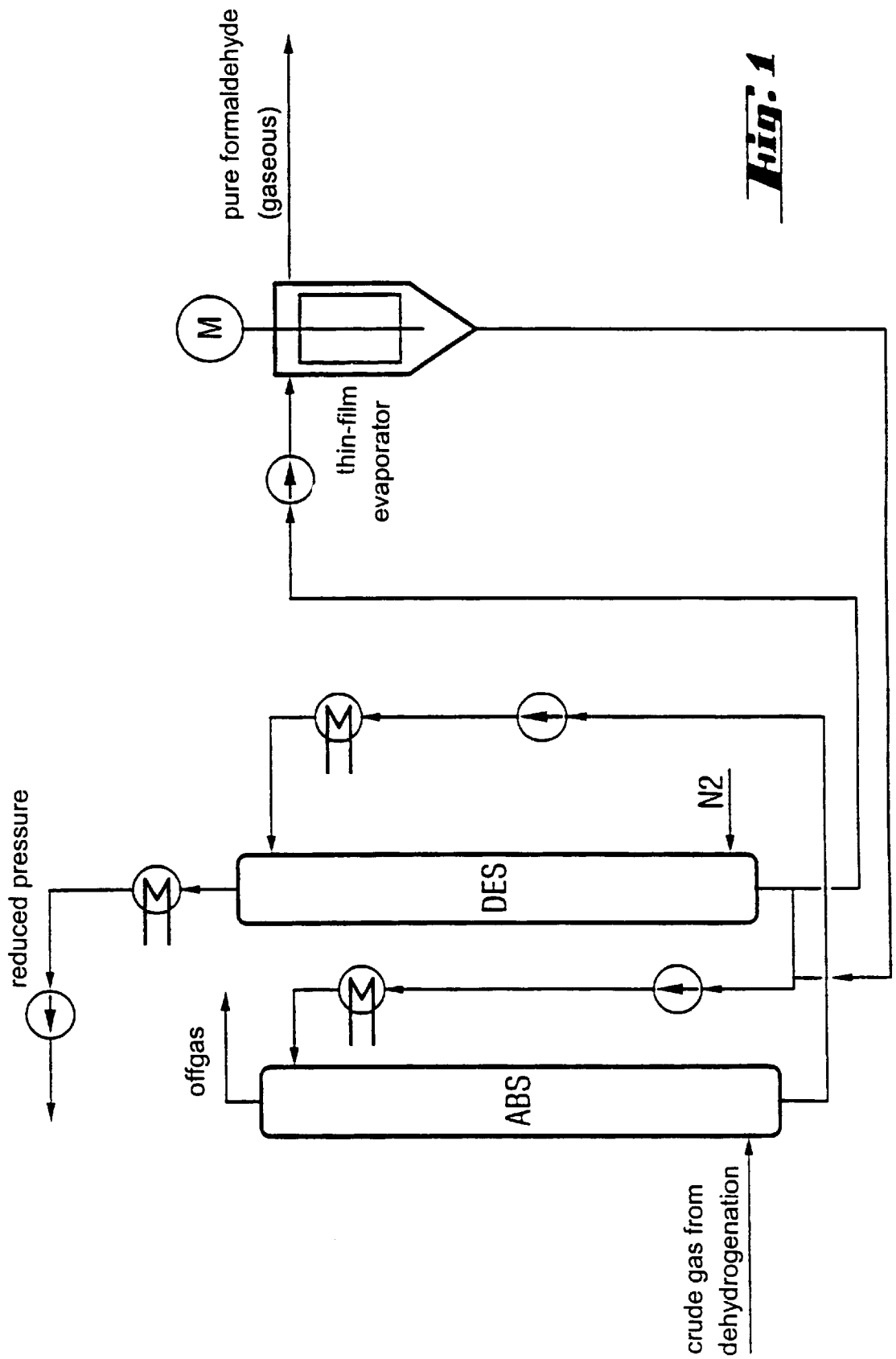

The alcohol/hemiformal solution discharged from the desorption unit and purified from impurities is then introduced via an introduction port into the pyrolysis unit (6) and there thermally cleaved. The alcohol formed in this process is recovered and, if appropriate with mixing with a part of the purified hemiformal of the desorption unit (4), recirculated to the absorption unit (1) for reuse. The pure formaldehyde is taken off as gaseous product stream (7) at the top end of the pyrolysis unit (6). The invention is described in more detail with reference to the examples below:

Example 1: HEMIFORMAL FORMATION IN THE ABSORPTION COLUMN

A formaldehyde/crude gas mixture is introduced at an inlet velocity of V=147 liters (S.T.P.)/hour and a temperature of 80°C into an apparatus as shown in FIG. 1, in which the absorption column (1) used is a laboratory scale plate column having a diameter of 50 mm and a height of 1.5 mm and 22 bubble-cap trays. In this case the absorption temperature is set via the scrubbing liquid input.

The effect of the absorption temperature and the liquid loading, ie. the circulation rate of the alcohol cyclohexanol, on the reaction of formaldehyde and selective separation of minor components is shown on the basis of five different experimental examples. In this case the circulation rate was between 10 I/hour (corresponding to a liquid loading of B=5m3 per m2 and hour) and 15 I/hour (corresponding to B=7.5 m3 per m2 and hour), the laboratory plate column used flooding at 20 I/hour. The inlet temperature of the scrubbing medium was varied between 0°C, 20°C and 40°C, as specified in Table 1.

TABLE 1

Variation of temperature and volumetric flow rate of the cyclohexanol

| Experiment | Volumetric flow rate [l/h] | Temperature [° C.] |
|---|---|---|
| 1 | 10 | 40 |
| 2 | 15 | 40 |
| 3 | 15 | 20 |
| 4 | 15 | 0 |
| 5 | 10 | 20 |

TABLE 2

Tabelle 2 reports the inlet and exit concentrations and the molar flow rates. The gas superficial flow rate was in this case approximately 0.02 m/sec and the ratio of liquid to gas stream molar flow rates was L/G = 95 mol/hour: 6.6 mol/hour = 14.4 mol/mol (density of cyclohexanol (CHol) at 20° C.: 952 kg/m$^3$, molar mass: 100.2 kg/kmol).

Experimental results (concentrations in the gas)

|  |  | total | Formaldehyde | Water | Methanol | Methyl formate |
|---|---|---|---|---|---|---|
| T = 40° C., V(CHol) = 10 l/h Experiment 6 | | | | | | |
| Crude gas feed (2) | ppm | | 270000 | 2000 | 300 | 1700 |
| | mol/h | 6.6 | 1.782 | 0.0122 | 0.00100 | 0.0101 |
| Offgas (3) | ppm | | 250000 | 1000 | 100 | 1300 |
| | mol/h | 4.9 | 0.1225 | 0.09490 | 0.000490 | 0.00637 |
| % in offgas | | | 6.9 | 37.1 | 24.8 | 63.1 |
| T = 40° C., V(CHol) = 15 l/h Experiment 7 | | | | | | |
| Crude gas feed (2) | ppm | | 270000 | 1000 | 150 | 1300 |
| | mol/h | 6.6 | 1.782 | 0.0066 | 0.00099 | 0.00883 |
| Offgas (3) | ppm | | 2000 | 600 | 90 | 600 |
| | mol/h | 4.9 | 0.098 | 0.00294 | 0.000441 | 0.00294 |
| % in offgas | | | 5.5 | 44.5 | 44.6 | 34.3 |
| T = 20° C., V(CHol) = 15 l/h Experiment 8 | | | | | | |
| Crude gas feed (2) | ppm | | 270000 | 1000 | 100 | 300 |
| | mol/h | 6.6 | 1.782 | 0.0066 | 0.00066 | 0.00198 |
| Offgas (3) | ppm | | 23000 | 300 | 70 | 220 |
| | mol/h | 4.9 | 0.1127 | 0.00147 | 0.000343 | 0.001078 |
| % in offgas | | | 6.3 | 22.3 | 52.0 | 54.4 |
| T = 0° C., V(CHol) = 15 l/h Experiment 9 | | | | | | |
| Crude gas feed (2) | ppm | | 270000 | 1000 | 100 | 300 |
| | mol/h | 6.6 | 1.782 | 0.0066 | 0.00066 | 0.00198 |
| Offgas (3) | ppm | | 23000 | 250 | 50 | 200 |
| | mol/h | 4.9 | 0.1127 | 0.001225 | 0.000245 | 0.00098 |
| % in offgas | | | 6.3 | 18.6 | 37.1 | 49.5 |

It can be seen from Table 2 that the reaction of formaldehyde is only dependent on temperature to a slight extent.

Table 3 reports the separation of the impurities based on formaldehyde with the laboratory column used.

Table 3: By-product separation and by-product selectivity in the absorption column (1), in cyclohexanol after an experimental period of 5.5 hours (experiment 6)

TABLE 3

By-product separation and by-product selectivity in the absorption column (1), in cyclohexanol after an experimental period of 5.5 hours (experiment 6)

| | in the crude gas | in the cyclohexanol | percentage depletion |
|---|---|---|---|
| Methanol to formaldehyde | 0.11% | 0.08% | 0.02 |
| Water to formaldehyde | 0.74% | 0.5% | 0.15 |
| Methyl formate to formaldehyde | 0.22% | 0.17% | 0.03 |

It must be observed here that in the process according to the invention, surprisingly, a purification occurs as soon as in the absorption unit (1), which leads to the fact that, if appropriate, the desorption unit (4) may be omitted with suitable process procedure in the absorption unit (1).

Example 2: SEPARATION OF THE IMPURITIES IN THE DESORPTION COLUMNS

The solutions obtained from the absorption unit (1) of Example 2 were introduced a desorption column (4) (DN-50 laboratory column of length 2m, having one meter each of Sulzer CY and Sulzer BX packings) according to FIG. 1 with the by-products additionally having been stripped by nitrogen under reduced pressure. The ts are reported in Table 4, the vacuum having been varied and the temperature having been set via the scrubbing solution.

TABLE 4

Gas concentration in the desorption stream
(Carrier gas: Nitrogen at 20 liter/hour)

| Experiment | Temperature [° C.] | Pressure [mbar] | Formaldehyde [ppm] | Water [ppm] | Methanol [ppm] | Methyl formate [ppm] |
|---|---|---|---|---|---|---|
| 10 | 26 | 40 | 380 | 8000 | 220 | 1800 |
| 11 | 26 | 40 | 500 | 15800 | 100 | 500 |
| 12 | 26 | 10 | 500 | 1500 | 70 | 300 |
| 13 | 26 | 10 | 380 | 1000 | 120 | 1000 |
| 14 | 01 | 20 | 140 | 2700 | 250 | 4000 |

Table 5 reports the molar ratios of water/methanol/methyl formate to formaldehyde the concentration factor (based on the crude mixture).

Table 5a: Water to formaldehyde ratio

TABLE 5a

Water to formaldehyde ratio

| Experiment | Desorption temp. [° C.] | Desorption pressure [mbar] | Water to formaldehyde in the crude gas | Water to formaldehyde in the desorption gas | Concentration factor |
|---|---|---|---|---|---|
| 15 | 40 | 80 | 1:270 | 1:4 | approx. 70 |
| 16 | 40 | 500 | 1:270 | 1:9 | approx. 30 |
| 17 | 10 | 500 | 1:270 | 1:11 | approx. 25 |
| 18 | 10 | 80 | 1:270 | 1:7 | approx. 40 |
| 19 | 20 | 40 | 1:270 | 1:3 | approx. 90 |

TABLE 5b

Methanol to formaldehyde ratio

| Experiment | Desorption temp. [° C.] | Desorption pressure [mbar] | Methanol to formaldehyde in the crude gas | Methanol to formaldehyde in the desorption gas | Concentration factor |
|---|---|---|---|---|---|
| 15 |    | 380 | 1:1800 | 1:36 | approx. 50 |
| 16 | 26 | 500 | 1:1800 | 1:70 | approx. 30 |
| 17 | 26 | 500 | 1:1800 | 1:79 | approx. 20 |
| 18 | 26 | 380 | 1:1800 | 1:58 | approx. 30 |
| 19 | 01 | 140 | 1:2250 | 1:40 | approx. 60 |

TABLE 5c

Methyl formate to formaldehyde ratio

| Experiment | Desorption temp. [° C.] | Desorption pressure [mbar] | Methyl formate to formaldehyde in the crude gas | Methyl formate to formaldehyde in the desorption gas | Concentration factor |
|---|---|---|---|---|---|
| 15 | 40 | 380 | 1:450 | 1:4.4 | approx. 100 |
| 16 | 406 | 500 | 1:450 | 1:14 | approx. 30 |
| 17 | 10 | 500 | 1:450 | 1:18 | approx. 25 |
| 18 | 10 | 80 | 1:450 | 1:7 | approx. 60 |
| 19 | 20 | 40 | 1:900 | 1:2.5 | approx. 300 |

A temperature as high as possible with a reduced pressure as low as possible is advantageous for lasting desorption of the by-products. The upper temperature limit established by evaporation of the scrubbing medium (cyclohexanol) and also by degradation reactions which themselves produce by-products. Advantageous conditions are 20 to 80°C at a reduced pressure of below 100 mbar, preferably ween 10 and 100 mbar. The cyclohexanol cleaned of by-products in this experimental structure was pyrolyzed in a thin-film evaporator (6) at temperatures between 120 and 180°C and pressure in the range from 50 to 1300 mbar.

We claim:

1. (Amended) A process for purifying formaldehyde in which formaldehyde is reacted with alcohol to form the hemiformal and the hemiformal thus formed is freed from unwanted feedstocks and synthesis by-products and/or impurities and the hemiformal thus purified is pyrolyzed to form formaldehyde, which comprises scrubbing the formaldehyde in an absorption unit with an alcohol having a boiling point markedly above the boiling point of water and markedly below the pyrolysis temperature of the hemiformal and [in this case]reacting [this virtually] the alcohol and formaldehyde completely to give the hemiformal and, simultaneously, separating it off, in a first separation step, from gaseous impurities not absorbed in the scrubbing solution, converting residual impurities into a gaseous state in a desorption unit, the desorption temperatures and desorption pressures employed being above the evaporation conditions of water and below the pyrolysis conditions of the hemiformal, and separating [them] off the residual impurities from the liquid hemiformal, cleaving the hemiformal thus purified to the alcohol and formaldehyde in a pyrolysis unit and recovering the alcohol and the formaldehyde, and wherein a temperature in the range from 15 to 40°C is maintained in the absorption column, and wherein desorption is carried out at temperatures in the range of 20 to 1°C and pyrolysis is carried out at temperatures in the range of 100 to 200°C.

2. The process as claimed in claim 1, wherein gaseous formaldehyde is used.

3. The process as claimed in claim 1, wherein the formaldehyde and the alcohol are introduced into the absorption column in countercurrent to one another.

4. The process as claimed in claim 1, wherein the alcohol used is cyclohexanol.

5. The process as claimed in claim 1, wherein, in the desorption unit, the impurities are separated off with heating and/or under reduced pressure and/or are stripped off using an auxiliary gas.

6. The process as claimed in claim 1, wherein the pyrolysis unit used is an evaporator.

7. The process as claimed in claim 1, wherein the formation of hemiformal in the absorption column is controlled via the scrubbing medium rate (volumetric flow rate of alcohol).

8. The process as claimed in claim 1, wherein the inert gas used in the desorption column is nitrogen.

9. The process as claimed in claim 1, wherein the desorption column is omitted and the hemiformal formed in the absorption unit is fed directly to the pyrolysis unit.

* * * * *

UNITED STATES PATENT AND TRADEMARK OFFICE
CERTIFICATE OF CORRECTION

PATENT NO. : 6,229,053 B1
DATED : May 8, 2001
INVENTOR(S) : Werner Slevers, Elke Schweers, and Christine Meister It is certified that error appears in the above-identified patent and that said Letters Patent is hereby corrected as shown below:

Column 3,
Line 65, "$10^{-2}$ Ns/m" should be -- $10^{-2}$ Ns/m$^2$ --.

Column 6,
Line 51, "B=5m3 per m2" should be -- B=5m$^3$ per m$^2$ --.
Line 52, "B=7.5 m3 per m2" should be -- B=7.5 m$^3$ per m$^2$ --.

Column 8,
Line 58, "introduced a" should be -- introduced into a --.
Line 62, "ts" should be -- results --.

Column 9,
Line 67, "ween" should be -- between --.

Column 10,
Line 17, after and insert -- a --.

Column 10,
Line 63, remove "(Amended)".

Column 11,
Line 4, remove "[in this case]" and "[this virtually]".
Line 12, remove "[them]".
Line 19, "1 °C" should be -- 100°C --.

Signed and Sealed this

Twelfth Day of March, 2002

Attest:

*Attesting Officer*

JAMES E. ROGAN
*Director of the United States Patent and Trademark Office*